(12) United States Patent
Katsuyama (10) Patent No.: US 10,918,355 B2
(45) Date of Patent: Feb. 16, 2021

(54) ULTRASOUND DIAGNOSTIC DEVICE AND ULTRASOUND DIAGNOSTIC METHOD

(71) Applicant: FUJIFILM Corporation, Tokyo (JP)

(72) Inventor: Kimito Katsuyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/730,379

(22) Filed: Dec. 28, 2012

(65) Prior Publication Data
US 2013/0116564 A1    May 9, 2013

Related U.S. Application Data (63) Continuation of application No. PCT/JP2011/064891, filed on Jun. 29, 2011.

(30) Foreign Application Priority Data

Jun. 30, 2010   (JP) ................................ 2010-150065

(51) Int. Cl.
  *A61B 8/08*   (2006.01)
  *A61B 8/00*   (2006.01)
  *A61B 8/14*   (2006.01)

(52) U.S. Cl.
  CPC .............. *A61B 8/08* (2013.01); *A61B 8/4444* (2013.01); *A61B 8/469* (2013.01); *A61B 8/5223* (2013.01); *A61B 8/145* (2013.01); *A61B 8/4488* (2013.01)

(58) Field of Classification Search
  None
  See application file for complete search history.

(56) References Cited

U.S. PATENT DOCUMENTS 4,592,237 A * 6/1986 Ogura .................... G01N 29/07
                                                              73/602
4,627,290 A   12/1986 Ogawa et al.
(Continued)

FOREIGN PATENT DOCUMENTS

EP    0181668 A1    5/1986
EP    2 177 164 A1  4/2010
(Continued)

OTHER PUBLICATIONS

2nd Office Action issued by the State Intellectual Property Office of China dated Dec. 16, 2014 in connection with Chinese Patent Application No. 201180032958.3.
(Continued)

*Primary Examiner* — Bill Thomson
*Assistant Examiner* — Shahdeep Mohammed
(74) *Attorney, Agent, or Firm* — Edwards Neils LLC; Jean C. Edwards, Esq.

(57) ABSTRACT

An ultrasound diagnostic device includes: an ultrasound probe including a plurality of ultrasound transducers transmitting ultrasound waves to an object and receiving ultrasound waves reflected from the object to output an ultrasound detection signal, a region-of-interest setting device setting a region of interest within the object, a transmission focus instructing device making the ultrasound probe transmit the ultrasound waves by focusing on the region of interest, a device setting at least one or more points of interest in the region of interest, a device finding a change in sound velocity or attenuation at the point of interest, and a device finding an index indicating a sonic variation or an attenuation variation based on the change in sound velocity or attenuation.

14 Claims, 4 Drawing Sheets

(56) References Cited

U.S. PATENT DOCUMENTS

| | | | |
|---|---|---|---|
| 4,830,015 A * | 5/1989 | Okazaki | 600/442 |
| 5,224,480 A | 7/1993 | Yamada et al. | |
| 5,465,723 A | 11/1995 | Angelsen et al. | |
| 5,531,117 A * | 7/1996 | Fortes | G01S 7/52049 |
| | | | 600/442 |
| 5,810,731 A | 9/1998 | Sarvazyan et al. | |
| 7,666,138 B2 * | 2/2010 | Ogawa | G01S 7/52047 |
| | | | 600/437 |
| 2005/0015010 A1 | 1/2005 | Antich et al. | |
| 2005/0070796 A1 | 3/2005 | Tsujita | |
| 2006/0241456 A1 * | 10/2006 | Karasawa | A61B 8/463 |
| | | | 600/447 |
| 2008/0275344 A1 * | 11/2008 | Glide-Hurst et al. | 600/442 |
| 2009/0112088 A1 * | 4/2009 | Ohuchi et al. | 600/438 |
| 2010/0040200 A1 * | 2/2010 | Ema et al. | 378/98.12 |
| 2010/0113932 A1 | 5/2010 | Antich et al. | |
| 2010/0256493 A1 | 10/2010 | Chono | |
| 2011/0245668 A1 * | 10/2011 | Tamura | A61B 8/08 |
| | | | 600/438 |
| 2013/0131511 A1 | 5/2013 | Peterson et al. | |

FOREIGN PATENT DOCUMENTS

| | | | |
|---|---|---|---|
| JP | 60-220051 A | | 11/1985 |
| JP | 61-025536 A | | 2/1986 |
| JP | 61-087538 A | | 5/1986 |
| JP | 03-024868 A | | 2/1991 |
| JP | 03-073136 A | | 3/1991 |
| JP | 04-035653 A | | 2/1992 |
| JP | 05-095946 A | | 4/1993 |
| JP | 05-111484 A | | 5/1993 |
| JP | 06-070929 A | | 3/1994 |
| JP | 06-105841 A | | 4/1994 |
| JP | 07-051270 A | | 2/1995 |
| JP | 2001-170046 A | | 6/2001 |
| JP | 2003-339698 A | | 12/2003 |
| JP | 2004-073697 A | | 3/2004 |
| JP | 2006-095002 | | 4/2006 |
| JP | 2006-122666 | | 5/2006 |
| JP | 2006-217934 A | | 8/2006 |
| JP | 2007-007045 | | 1/2007 |
| JP | 2010-193944 A | | 9/2010 |
| WO | WO2007/110375 | * | 4/2007 |
| WO | WO 2008/139245 A1 | * | 11/2008 |
| WO | 2009/060751 A1 | | 5/2009 |
| WO | WO 2009/060751 | * | 5/2009 |

OTHER PUBLICATIONS

Notification of Reasons for Rejection, issued by Japanese Patent Office dated Feb. 3, 2015 in connection with Japanese Patent Application No. 2012-522653.

Notification of Reasons for Rejection issued by the Japanese Patent Office (JPO) dated Jan. 23, 2015 in connection with Japanese Patent Application No. 2012-522652.

Wang Zhigang: Study, Application and Development of Ultrasonic Tissue Characterization, Chinese Journal of Medical Imaging, Jan. 20, 1999, vol. 15, Issue 1, pp. 70-72.

Second Office Action issued by State Intellectual Property Office (SIPO) of China dated Dec. 10, 2014 in connection with Chinese Patent Application No. 201180032787.4.

International Preliminary Report on Patentability (IPRP), which dated Feb. 12, 2013 in connection with PCT/JP2011/064890.

Hachiya H., "Acoustic Characteristics of the Tissue and the Ultrasonic B-mode Image", Medical Imaging Technology, 2003, pp. 95-100, vol. 21 No. 2.

Akamatsu K., "Tissue Characterization by Sound Speed Measurement", Rinshoi (Journal of Clinical Medicine), 1986, pp. 104-108, vol. 12, No. 11.

Maruzen, "Medical Ultrasound Wave—Ultrasound Wave in Living Body", Cho-onpa Binran (Handbook of Ultrasonic Wave), 1999, pp. 420-423.

Non-Final Office Action issued in co-pending U.S. Appl. No. 13/730,231 dated May 29, 2015.

International Search Report and Written Opinion issued in PCT/JP2011/064890 dated Sep. 6, 2011.

Advisory Action issued by the USPTO dated May 23, 2016 in connection with co-pending U.S. Appl. No. 13/730,231.

Non-Final Office Action issued by the USPTO dated Oct. 25, 2016 in connection with co-pending U.S. Appl. No. 13/730,231.

Advisory Action issued by the USPTO dated Dec. 15, 2017 in connection with co-pending U.S. Appl. No. 13/730,231.

Final Office Action issued by the USPTO dated Jun. 14, 2017 in connection with co-pending U.S. Appl. No. 13/730,231.

Non-Final Office Action issued by the USPTO dated Jul. 12, 2018 in connection with co-pending U.S. Appl. No. 13/730,231.

Final Office Action issued by the USPTO dated Feb. 27, 2019 in connection with co-pending U.S. Appl. No. 13/730,231.

Advisory Action issued by the USPTO dated Jun. 26, 2019 in connection with co-pending U.S. Appl. No. 13/730,231.

Non Final Office Action issued by the USPTO dated Mar. 19, 2020 in connection with co-pending U.S. Appl. No. 13/730,231.

* cited by examiner

ULTRASOUND DIAGNOSTIC DEVICE AND ULTRASOUND DIAGNOSTIC METHOD

CROSS-REFERENCE TO RELATED APPLICATIONS

This application is a continuation application and claims the priority benefit under 35 U.S.C. § 120 of PCT Application No. PCT/JP2011/064891 filed on Jun. 29, 2011, which was published under PCT Article 21(2) in Japanese, which application designates the U.S., and also claims the priority benefit under 35 U.S.C. § 119 of Japanese Patent Application No. 2010-150065 filed on Jun. 30, 2010, which applications are all hereby incorporated by reference in their entireties.

TECHNICAL FIELD

The present invention relates to ultrasound diagnostic devices and ultrasound diagnostic methods and, in particular, to an ultrasound diagnostic device and ultrasound diagnostic method in which an ultrasound image of a site of an object to be diagnosed is shot and displayed by using ultrasound waves and a tissue characteristic of the object is diagnosed based on change of sound velocity or attenuation of the ultrasound waves in a region of interest of the object.

BACKGROUND ART

An ultrasound diagnostic device has conventionally been known that shoots and displays an ultrasound image of a site of an object to be diagnosed by using ultrasound waves, and various attempts have been made to measure acoustic characteristics such as sound velocity, attenuation, scattering, or the like of the ultrasound to utilize diagnoses, such as characteristic diagnosis of the inner structure and components of an object's tissue and discrimination of a tissue or a lesion.

For example, Patent Literature 1 discloses a sonic measuring method as described below. Irradiation with an ultrasound wave is made as the angle of irradiation of a transmission transducer is varied and is received as the incident angle of a reception transducer is varied, and an elapsed time between irradiation and reception is measured and stored in memory. On the other hand, based on a virtual sound velocity distribution stored in a sonic memory, the angles of transmission and reception waves of the transmission transducer and the reception transducer are varied on the sonic memory to set respectively corresponding sound line paths. Each required time and the elapsed time previously stored in the memory are compared to find error data. The sound velocity distribution stored in the sonic memory is corrected so that the error data is minimum. With the corrected sound velocity distribution, a sound velocity is found.

Also, Patent Literature 2 discloses a method of extracting and rendering information associated with propagation attenuation inside a living body by taking a spatial difference between band-split detection signals near a depth of interest.

CITATION LIST

Patent Literature

PTL 1: Japanese Patent Application Laid-Open No. 5-95946
PTL 2: Japanese Patent Application Laid-Open No. 7-51270

SUMMARY OF INVENTION

Technical Problem

However, it has been reported that the conventional method of measuring a sound velocity or attenuation described above is macroscopic and, depending on the type of lesion, it is difficult for this macroscopic acoustic characteristic measuring method to grasp microscopic changes in acoustic characteristics.

Figure 4:
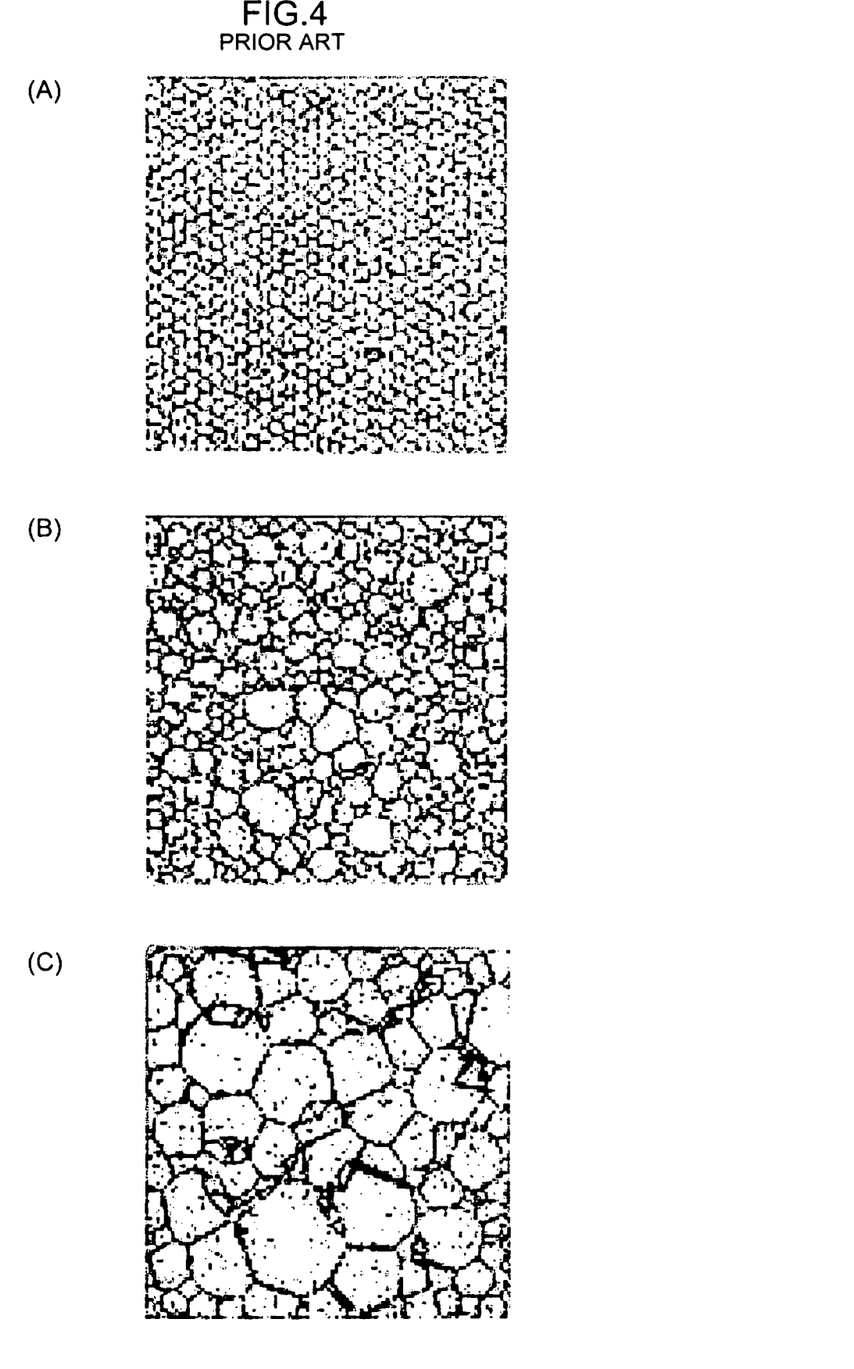

For example, according to Hiroyuki Hachiya, "Acoustic Characteristics of the Tissue and the Ultrasonic B-mode Image" (Medical Imaging Technology, vol. 21, No. 2, March 2003), when the liver suffers from cirrhosis and if liver cirrhosis develops, postnecrotic tissues are coupled together and their surrounding tissues become fibrous to form a node, thereby replacing a hepatic lobule by a reproduced node. For example, FIG. 4 depicts an example of the arrangement of scatterers. In FIG. 4, (a) depicts a normal liver, and each hepatic lobule structure has a random size on the order of 1.0 mm to 1.5 mm. In a moderate case of liver cirrhosis as depicted in (b) of FIG. 4, a plurality of hepatic lobule structures are destroyed to form fibrous tissues, and each node diameter grows to 3 mm to 4 mm. In a serious case of liver cirrhosis as depicted in (c) of FIG. 4 after the lesion develops, the node diameter grows to approximately 7 mm at maximum. It has been reported that a microscopic change in sound velocity structure occurs in a manner such that the sound velocity, attenuation, and scattering inside the nodes are lower than those of the normal liver and, conversely, those of the fibrous portion are higher than those of the normal liver. By contrast, however, according to Koichi Akamatsu, "Tissue Characterization by measurement of sound velocity" (Clinical Doctor, vol. 12, no. 11, 1986), it has been reported that there is no significant difference between macroscopic sound velocity values of the normal liver and the cirrhotic liver.

Therefore, the conventionally-suggested macroscopic method of measuring sound velocity or attenuation has a problem in which there is a possibility of being unable to grasp a microscopic change in structure of sound velocity or attenuation as described above.

The present invention was made in view of these circumstances, and has an object of providing an ultrasound diagnostic device and ultrasound diagnostic method capable of grasping a microscopic change in structure of sound velocity or attenuation due to a pathological change, the change being difficult to grasp with conventional measurement of an absolute value of sound velocity or attenuation.

Solutions to Problems

To achieve the object above, a first aspect of the present invention is directed to an ultrasound diagnostic device including an ultrasound probe including a plurality of ultrasound transducers transmitting ultrasound waves to an object and receiving ultrasound waves reflected from the object to output an ultrasound detection signal, a region-of-interest setting device setting a region of interest within the object, a device setting at least one or more points of interest in the region of interest, a device finding a change in sound velocity or attenuation at the point of interest, and a device finding an index indicating a sonic variation or an attenuation variation based on the change in sound velocity or attenuation.

With this, it is possible to grasp a microscopic change in structure of sound velocity or attenuation due to a pathological change, the change being difficult to grasp with measurement of an absolute value of sound velocity or attenuation, and a tissue characteristic can be easily diagnosed.

Also, a second aspect of the present invention is directed to the ultrasound diagnostic device according to the first aspect, further including a transmission focus instructing device making the ultrasound probe transmit the ultrasound waves by focusing on the region of interest.

Furthermore, in a third aspect of the present invention, the transmission focus instructing device judges an effective region of each transmission focus in advance.

With this, the process of finding a sound velocity can be performed at high speed.

Still further, in a fourth aspect of the present invention, the sound velocity at the point of interest is an environmental sound velocity.

Still further, in a fifth aspect of the present invention, the sound velocity at the point of interest is a local sound velocity in the region of interest.

Still further, in a sixth aspect of the present invention, the index is a standard deviation of magnitudes of the sonic variation or the attenuation variation.

Also, to achieve the object above, a seventh aspect of the present invention is directed to an ultrasound diagnostic method including a region-of-interest setting step of setting a region of interest within an object, a transmission focus instructing step of making the ultrasound probe transmitting the ultrasound waves by focusing on the region of interest, a step of setting at least one or more points of interest in the region of interest, a step of finding a change in sound velocity or attenuation at the point of interest, and an index calculating step of calculating an index indicating a sonic variation or an attenuation variation based on the change in sound velocity or attenuation, a characteristic diagnosing step of diagnosing a tissue characteristic based on the calculated index.

With this, it is possible to grasp a microscopic change in structure of sound velocity or attenuation due to a pathological change, the change being difficult to grasp with measurement of an absolute value of sound velocity or attenuation, and a tissue characteristic can be easily diagnosed.

Also, in an eighth aspect of the present invention, in the transmission focus instructing step, an effective region of each transmission focus is judged in advance.

With this, the process of finding a sound velocity can be performed at high speed.

Furthermore, in a ninth aspect of the present invention, the sound velocity at the point of interest is an environmental sound velocity.

Still further, in a tenth aspect of the present invention, the sound velocity at the point of interest is a local sound velocity in the region of interest.

Advantageous Effects of Invention

As described above, according to the present invention, it is possible to grasp a microscopic change in structure of sound velocity or attenuation due to a pathological change, the change being difficult to grasp with measurement of an absolute value of sound velocity or attenuation, and a tissue characteristic can be easily diagnosed.

BRIEF DESCRIPTION OF DRAWINGS

In FIG. 2, (a) to (c) are diagrams schematically describing processes of measuring a sonic variation or an attenuation variation.

In FIG. 4, (a) to (c) are diagrams for describing changes in tissue characteristics in liver cirrhosis.

DESCRIPTION OF EMBODIMENTS

The ultrasound diagnostic device and ultrasound diagnostic method according to the present invention are described in detail below with reference to the attached drawings.

Figure 1:
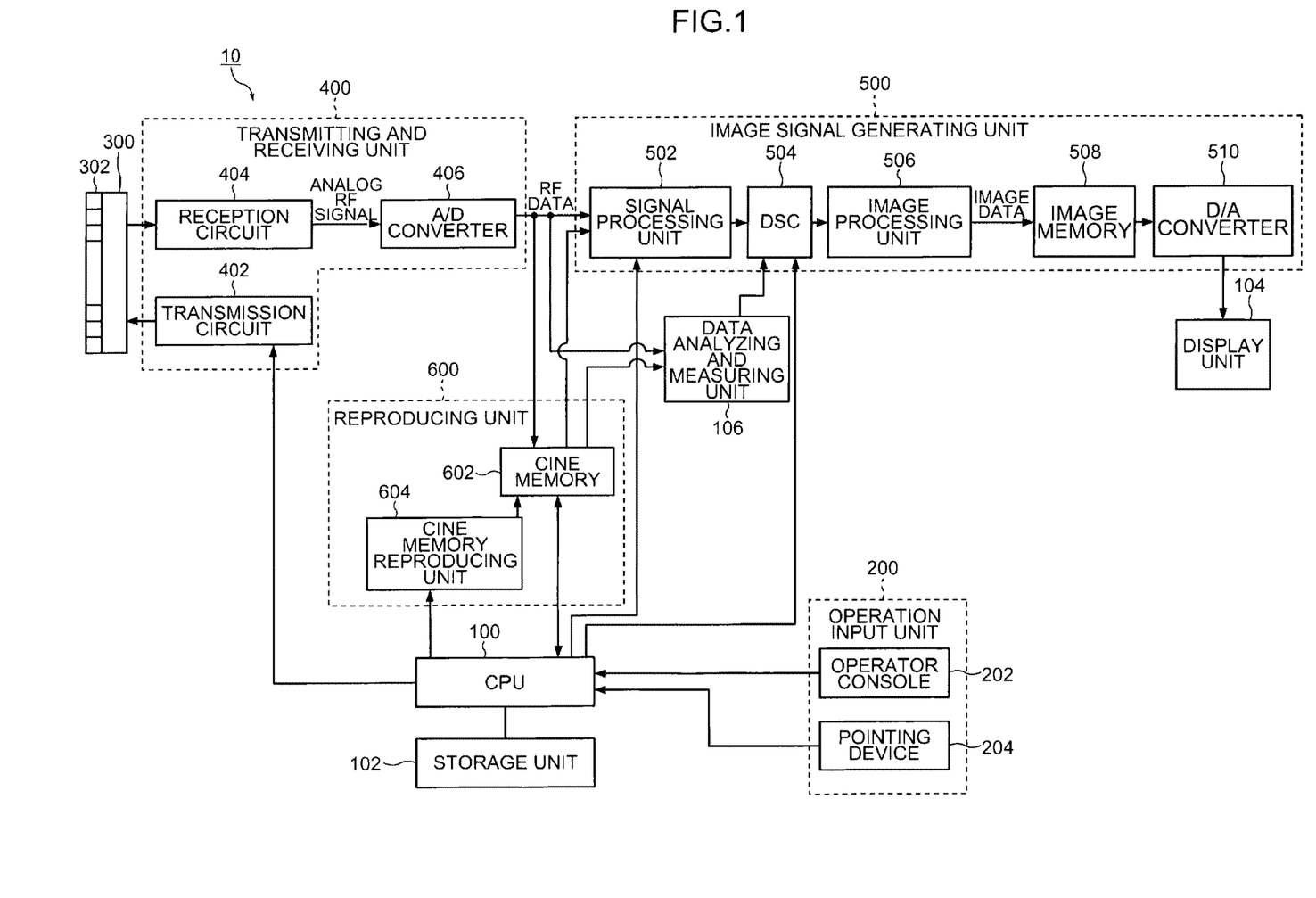
FIG. 1 is a block diagram of a schematic structure of an ultrasound diagnostic device according to an embodiment of the present invention.

FIG. 1 is a block diagram of a schematic structure of an ultrasound diagnostic device according to an embodiment of the present invention.

As depicted in FIG. 1, an ultrasound diagnostic device 10 of the present embodiment is a device in which an ultrasound beam is transmitted from an ultrasound probe 300 to an object OBJ, an ultrasound beam (an ultrasound echo) reflected from the object OBJ is received, and an ultrasound image is generated from a detection signal of the ultrasound echo for display.

A CPU (Central Processing Unit) 100 controls each block of the ultrasound diagnostic device 10 according to an operation input from an operation input unit 200.

The operation input unit 200 is an input device accepting an operation input from an operator, and includes an operation console 202 and a pointing device 204. The operation console 202 includes a keyboard accepting an input of character information (for example, patient information), a display mode switching button for switching a display mode between a mode of singly displaying an amplitude image (B-mode image) and a mode of displaying a judgment result of a local sound velocity value, a freeze button for making an instruction for switching between a live mode and a freeze mode, a cine memory reproducing button for making an instruction for cine memory reproduction, and an analysis and measurement button for making an instruction for analysis and measurement of an ultrasonic image. The pointing device 204 is a device accepting an input designated in a region on a screen of a display unit 104, and is, for example, a track ball or a mouse. Note that a touch panel can be used as the pointing device 204.

A storage unit 102 is a memory device having a control program for causing the CPU 100 to control each block of the ultrasound diagnostic device 10, and is, for example, a hard disk or a semiconductor memory.

The display unit 104 is, for example, a CRT (Cathode Ray Tube) display or a liquid-crystal display, displaying an ultrasound image (a moving picture and a still picture) and various setting screens.

An ultrasonic probe 300 is a probe for use as being brought to abut on the object OBJ, and includes a plurality of ultrasound transducers 302 configuring a one-dimensional or two-dimensional transducer array. The ultrasound transducers 302 each transmit an ultrasound beam to the object OBJ based on a drive signal applied from a transmission circuit 402, and receive an ultrasound echo reflected from the object OBJ to output a detection signal.

The ultrasound transducers 302 each include a transducer configured to have electrodes at both ends of a material having piezoelectricity (a piezoelectric element). As an example of the piezoelectric element configuring this transducer, a piezoelectric ceramic made of PZT (Pb (lead) zirconate titanate) or a high polymer piezoelectric element made of PVDF (polyvinylidene difluoride) or the like can be used. When an electrical signal is transmitted to the electrodes of the transducer described above to apply a voltage, the piezoelectric element expands and contracts and, with this expansion and contraction of the piezoelectric element, an ultrasound wave is generated at each transducer. For example, when a pulse-shaped electrical signal is transmitted to the electrodes of the transducer, a pulse-shaped ultrasound wave is generated. Also, when a continuous-wave electrical signal is transmitted to the electrodes of the transducer, a continuous-wave electrical signal is generated. Then, the ultrasound waves generated at the respective transducers are combined to form an ultrasound beam. Also, when an ultrasound wave is received by each transducer, the piezoelectric element of each transducer expands and contracts to generate an electrical signal. The electrical signal generated at each transducer is outputted as a detection signal of the ultrasound wave to a reception circuit 404.

Note that elements of a plurality of types with different ultrasonic conversion schemes can also be used as the ultrasonic transducers 302. For example, a transducer configured of the piezoelectric element described above may be used as an element for transmitting an ultrasound wave, and an ultrasound transducer of an optical detection scheme may be used as an element for receiving an ultrasound wave. Here, the ultrasound transducer of the optical detection scheme converts an ultrasound signal to an optical signal, and may be, for example, a Fabry-Perot resonator or a fiber Bragg grating. Next, an ultrasound diagnostic process in a live mode is described. The live mode is a mode for displaying and analyzing and measuring an ultrasonic image (moving picture) obtained by bringing the ultrasound probe 300 to abut on the object OBJ for transmission and reception of an ultrasound wave.

When the ultrasound probe 300 is brought to abut on the object OBJ and an ultrasound diagnosis starts upon an input of an instruction from the operation input unit 200, the CPU 100 outputs a control signal to the transmitting and receiving unit 400 to start transmission of an ultrasound beam to the object OBJ and reception of an ultrasound echo from the object OBJ. The CPU 100 sets a transmitting direction of the ultrasound beam and a receiving direction of the ultrasound echo for each ultrasound transducer 302.

Furthermore, the CPU 100 selects a transmission delay pattern according to the transmitting direction of the ultrasound beam and also selects a reception delay pattern according to the receiving direction of the ultrasound echo. Here, the transmission delay pattern is pattern data of delay time to be given to a drive signal in order to form an ultrasound beam in a desired direction from the ultrasound waves transmitted from the plurality of ultrasound transducers 302, and the reception delay pattern is pattern data of delay time of reception of the plurality of ultrasound transducers 302. The transmission delay pattern and reception delay pattern described above are stored in advance in the storage unit 102. The CPU 100 selects the transmission delay pattern and the reception delay pattern from those stored in the storage unit 102 and outputs a control signal to the transmitting and receiving unit 400 according to the selected transmission delay pattern and reception delay pattern to control transmission and reception of ultrasonic waves.

The transmission circuit 402 generates a drive signal according to the control signal from the CPU 100 and applies the drive signal to the ultrasound transducers 302. Here, the transmission circuit 402 delays the drive signal to be applied to each of the ultrasound transducers 302 based on the transmission delay pattern selected by the CPU 100.

Here, the transmission circuit 402 performs transmission focus in which the timing of applying a drive signal to each of the ultrasound transducers 302 is adjusted (delayed) so that the ultrasound waves transmitted from the plurality of ultrasound transducers 302 form an ultrasound beam. Note that the timing of applying a driving signal may be adjusted so that the ultrasound waves transmitted at one time from the plurality of ultrasound transducers 302 arrive at an entire imaging region of the object OBJ.

The reception circuit 404 receives and amplifies an ultrasound detection signal outputted from each of the ultrasound transducers 302. As described above, since a distance between each of the ultrasound transducers 302 and an ultrasound reflection source inside the object OBJ is varied, the time when a reflected wave arrives at each of the ultrasound transducers 302 is varied. The reception circuit 404 includes a delay circuit that delays each detection signal by a difference (a delay time) in arrival time of the reflected wave according to the reception delay pattern set based on a sound velocity selected by the CPU 100 (hereinafter referred to as a virtual sound velocity) or a sound velocity distribution. Next, the reception circuit 404 performs matching and addition of the detection signals provided with the delay time, thereby performing a reception focus process. If another ultrasound reflection source is present at a position different from a ultrasound reflection source XROI, an ultrasound detection signal from that other ultrasound reflection source has a different arrival time. Thus, with addition at an addition circuit of the reception circuit 404 described above, the phase of the ultrasound detection signal from the other ultrasound reflection source is cancelled out. With this, the received signal from the ultrasound reflection source XROI is maximum, thereby achieving a focus. With the reception focus process described above, a sound ray signal with the ultrasound echo in focus (hereinafter referred to as an RF signal) is formed.

An A/D converter 406 converts an analog RF signal outputted from the reception circuit 404 to a digital RF signal (hereinafter referred to as RF data). Here, the RF data contains phase information of a received wave (a carrier wave). The RF data outputted from the A/D converter 406 is inputted to a signal processing unit 502 and a cine memory 602.

The cine memory 602 sequentially stores the RF data inputted from the A/D converter 406. The cine memory 602 also stores information regarding a frame rate (for example, a depth of the ultrasound wave at a reflection point, a density of scanning lines, and a parameter indicating a visual field width) inputted from the CPU 100 in association with the RF data described above.

The signal processing unit 502 performs STC (Sensitivity Time gain Control) to correct attenuation of the RF data described above due to distance according to the depth of the ultrasound wave at the reflecting point, and then performs an envelope detecting process to generate B-mode image data (image data representing the amplitude of the ultrasound echo with brightness (luminance) of dots).

The B-mode image data generated by the signal processing unit 502 is obtained by a scanning scheme different from a normal television signal scanning scheme. For this reason, a DSC (Digital Scan Converter) 504 performs conversion (raster conversion) of the B-mode image data described above to normal image data (for example, image data of a television signal scanning scheme (NTSC scheme)). An image processing unit 506 performs various necessary image processes (for example, a gray-scale process) on the image data inputted from the DSC 504.

An image memory 508 stores the image data inputted from the image processing unit 506. The D/A converter 510 converts the image data read from the image memory 508 to an analog image signal for output to the display unit 104. With this, an ultrasound image (a moving picture) shot by the ultrasound probe 300 is displayed on the display unit 104.

Note that while the detection signal subjected to the reception focus process at the reception circuit 404 is taken as an RF signal a detection signal not subjected to the reception focus process may be taken as an RF signal. In this case, a plurality of ultrasound detection signals outputted from the plurality of ultrasound transducers 302 are amplified at the reception circuit 404, and the amplified detection signals, that is, the RF signals, are subjected to A/D conversion at the A/D converter 406 to generate RF data. And, the RF data described above is supplied to the signal processing unit 502 and also stored in the cine memory 602. The reception focus process is digitally performed at the signal processing unit 502.

Next, a cine memory reproduction mode is described. The cine memory reproduction mode is a mode of displaying and analyzing and measuring an ultrasound diagnostic image based on the RF data stored in the cine memory 602.

When the cine memory reproducing button of the operation console 202 is pressed, the CPU 100 switches the operation mode of the ultrasound diagnostic device 10 to the cine memory reproduction mode. In the cine memory reproduction mode, the CPU 100 instructs the cine memory reproducing unit 604 to reproduce the RF data specified by an operation input from the operator. Based on the instruction from the CPU 100, the cine memory reproducing unit 604 reads the RF data from the cine memory 602 for transmission to the signal processing unit 502 of an image signal generating unit 500. The RF data transmitted from the cine memory 602 is subjected to a predetermined process (the process similar to that in the live mode) at the signal processing unit 502, the DSC 504 and the image processing unit 506 to be converted to image data, and is then outputted via the image memory 508 and the D/A converter 510 to the display unit 104. With this, an ultrasound image (a moving picture or a still picture) based on the RF data stored in the cine memory 602 is displayed on the display unit 104.

In the live mode or the cine memory reproduction mode, when the freeze button of the operation console 202 is pressed while the ultrasound image (the moving picture) is being displayed, the ultrasound image displayed at the time of pressing the freeze button is displayed as a still picture on the display unit 104. With this, the operator can cause the still picture of a region of interest (ROI) to be displayed for observation.

When the measurement button on the operation control 202 is pressed, analysis and measurement specified by the operation input from the operator is performed. When the measurement button is pressed in each operation mode, a data analyzing and measuring unit 106 obtains the RF data before subjected to the image processing from the A/D converter 406 or the cine memory 602 and, by using the RF data, performs the analysis and measurement specified by the operator (for example, a distortion analysis of a tissue part (a hardness analysis), blood flow measurement, measurement of a motion of a tissue part, or measurement of an IMT (Intima-Media Thickness) value). Also, he data analyzing and measuring unit 106 performs a process of measuring a local sound velocity value or calculating an index indicting a variation in sound velocity or attenuation, details of which will be described further below. The analysis and measurement results from the data analyzing and measuring unit 106 are outputted to the DSC 504 of the image signal generating unit 500. The DSC 504 causes the data analyzing and measuring unit 106 to insert the analysis and measurement results into image data of the ultrasound image for output to the display unit 104. With this, the ultrasound image and the analysis and measurement results are displayed on the display unit 104.

Also, when the display mode switching button is pressed, the display mode is switched among a mode for displaying the B-mode image alone, a mode for displaying the judgment results regarding a local sound velocity value as superposed on the B-mode image (for example, a display as being colored or with varied luminance according to the local sound velocity value or a display with points having the same local sound velocity value connected to each other), and a mode for displaying the B-mode image and an image of the judgment results regarding the local sound velocity value arranged in a tiled manner. With this, the operator can observe the judgment results regarding the local sound velocity value to discover a lesion, for example.

Note that based on the judgment results regarding the local sound velocity value, the B-mode image obtained by performing at least one of a transmission focus process and a reception focus process may be displayed on the display unit 104.

The operation of the ultrasound diagnostic device 10 of the present embodiment is described below.

In the present invention, a region of interest is set, a sonic variation or an attenuation variation is evaluated based on a change in position of a sound velocity value or an attenuation value found in the region of interest, and the evaluation is used for diagnosis of a tissue characteristic.

Figure 2:
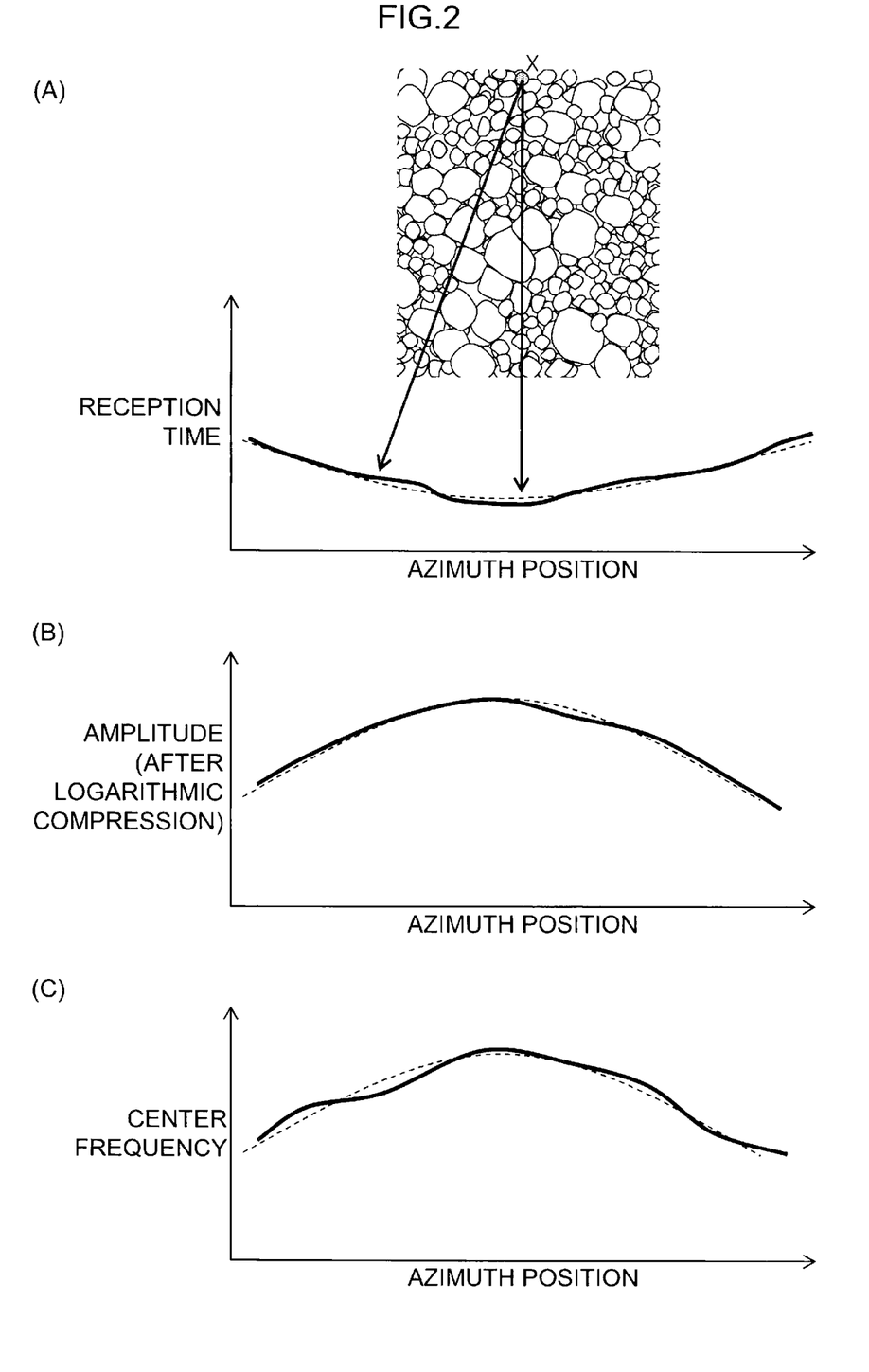

FIG. 2 schematically depicts processes of measuring a sonic variation and an attenuation variation.

In FIG. 2, (a) depicts reception time, (b) depicts amplitude, and (c) depicts center frequency. In each drawing, a graph representing a variation in azimuth position occurring from a microscopic structure of sound velocity or attenuation of a target is indicated by a solid line, and a graph when sound velocity or attenuation of the target is regarded as being constant is indicated by a broken line.

As depicted in FIG. 2, the reception time, amplitude, and center frequency of the received wave of pseudo point reflection formed by performing transmission focus have a variation from the reception time, amplitude, and center frequency obtained by assuming constant sound velocity and constant attenuation.

A microscopic structure of sound velocity or attenuation causes a variation in reception time, amplitude, and center frequency because media having different sound velocities and attenuations are present in a mixed manner on a microscopic scale and the mixture ratio is varied depending on the path corresponding to each azimuth position.

Also, since the reception time, amplitude, and center frequency are varied differently depending on the pseudo point reflection position and also the transmission path is varied, a macroscopic sound velocity of attenuation value (sound velocity or attenuation regarded as being constant) found from the reception time, amplitude, or center frequency is varied depending on the point reflection position.

Here, it can be easily found from FIG. 2 that as a change in microscopic sound velocity and attenuation is larger, a variation in azimuth position of the reception time, amplitude, and center frequency is larger and, also, as a spatial frequency of a change in microscopic sound velocity and attenuation is larger, a spatial frequency of a change in azimuth position of the reception time, amplitude, and center frequency is larger. And, it can be found that as a variation in reception time, amplitude, and center frequency is larger, a variation due to the point reflection position of the microscopic sound velocity and attenuation value found therefrom is larger, or as a spatial frequency of a variation in reception time, amplitude, and center frequency is larger, a spatial frequency of the microscopic sound velocity and attenuation value found therefrom is larger.

Therefore, from the variation due to the position of the macroscopic sound velocity or attenuation measurement value in the region of interest, information about the microscopic sound velocity or attenuation structure can be obtained.

With this, by judging a variation in sound velocity or attenuation, this can be used for diagnosis of a tissue characteristic. Note that while liver cirrhosis has been taken as an example for description herein, it is clear that the present invention can be applied to any, without being restricted to the case of liver cirrhosis.

A process of finding an index (a variation index) indicating a sonic variation or an attenuation variation is described below.

Figure 3:
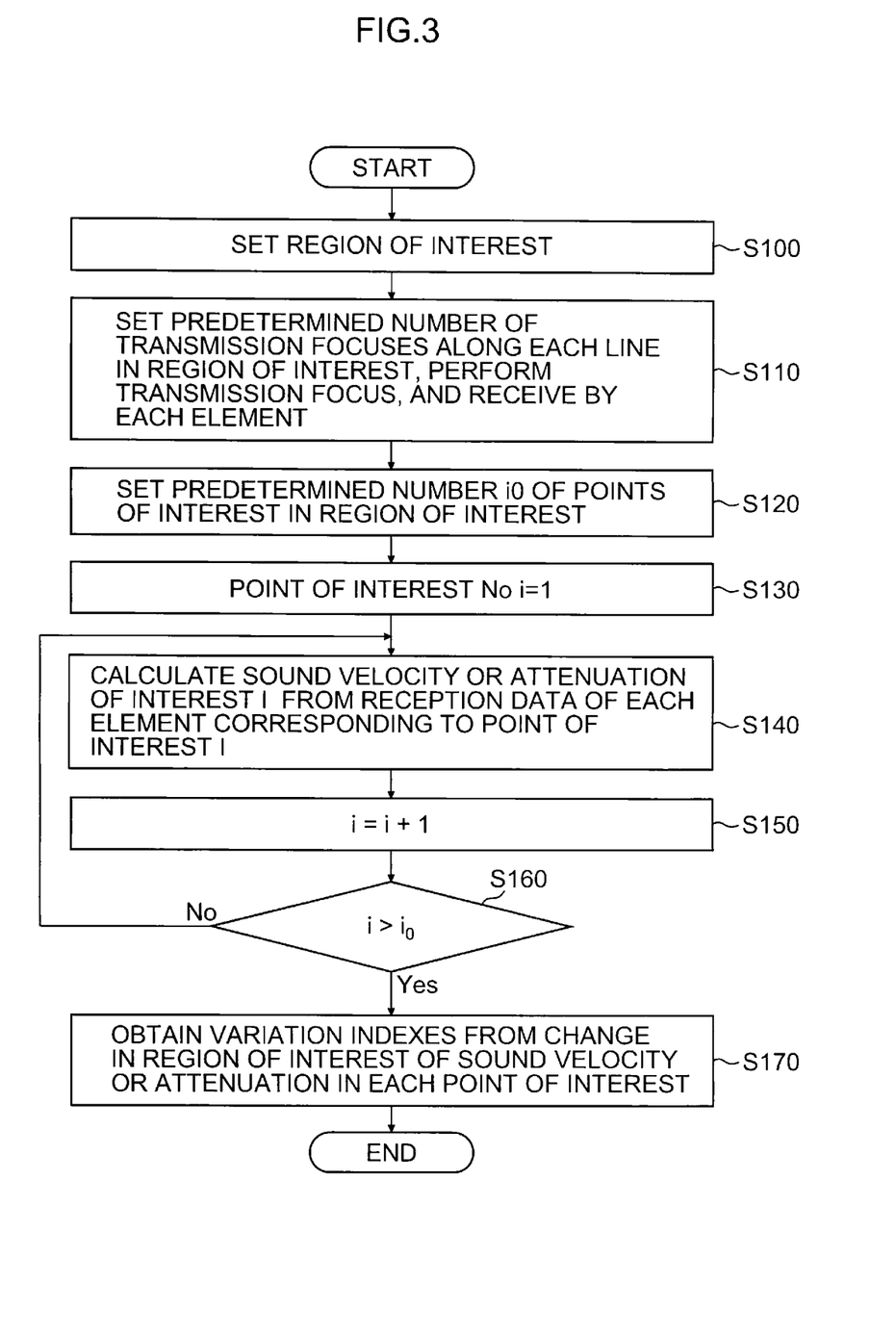
FIG. 3 is a flowchart of a flow of a process of finding a variation index of sound velocity or attenuation.

FIG. 3 is a flowchart of a flow of a process of finding a variation index of sound velocity or attenuation.

First, a region of interest is set at step S100 of FIG. 3.

Next, at step S110, a predetermined number of transmission focuses are set along each line in the region of interest, relevant transmission focus is performed, and reception is made by each element.

Here, to select a transmission focus corresponding to each point of interest, an effective region of each transmission focus may be judged in advance as follows.

That is, a transmission focus No i is first set, a line No j is selected in a specified line width for a predetermined specified line No, and each element's received signal of the focus No i and the line No j is read. Next, a set sound velocity No k is set, reception focus with the set sound velocity No k is performed on the received signal of the line No j of the transmission focus No i, and an index or image is stored. This process is repeatedly performed with the set sound velocity No being varied. When processes with predetermined set sound velocities are completed, the line No is changed within the specified line width, and reception focus is performed again on a new line No with the set sound velocity No k being varied as described above, and an index or image is stored.

Next, an environmental sound velocity (an average sound velocity) of each depth is found from the indexes or images in all lines within the specified line with with each set sound velocity, a standard deviation of environment sound velocities in a depth direction is calculated, a minimum point is judged as an actual focus depth, and an effective region of the transmission focus No i is found. Then, the transmission focus No is changed, and an effective region for the next transmission focus No is found in the same manner as above.

Note that transmission focus is performed correspondingly to each point of interest.

Next, at step S120, a predetermined number ($i_0$) of points of interest are (is) set in the region of interest. The number of points of interest may be one, that is, the predetermined number $i_0$ may be 1.

Then, for each $i_0$ points of interest, a sound velocity or attenuation at that point of interest is found.

First, at step S130, i indicating a point-of-interest number is set at 1 (i=1).

Then, at step S140, each element's received data of transmission focus corresponding to an i-th point of interest is selected, and a sound velocity or attenuation at the i-th point of interest is found from the relevant data.

How to find that data is not particularly restrictive and, for example, a known method as described below may be used.

For example, as a method of finding a sound velocity when an environmental sound velocity (an average sound velocity) is used as a sound velocity at the point of interest, an image analyzing scheme has been known (for example, refer to Japanese Patent Application Laid-Open No. 2007-7045) in which a sound velocity value is found so that characteristics such as sharpness and contrast of an image of the region of interest are maximum.

Here, a sound velocity assumed for setting a delay time is referred to a set sound velocity, and an intensity distribution of ultrasonic intensity with respect to an azimuth direction is referred to as a beam profile. And, a plurality of beam profiles with different set sound velocities are generated from an echo signal obtained by phasing and adding by the reception circuit, and the generated plurality of beam profiles are superposed on the same screen for display. A set sound velocity of a beam profile corresponding to a minimum beam width among the plurality of beam profiles with different set sound velocities is assumed as a biological sound velocity.

Alternatively, a graph representing a change in beam width due to the set sound velocity may be generated, a minimum value of an approximate curve obtained by approximating the change with a high-level curve may be extracted, and then a set sound velocity corresponding to that minimum value may be assumed as an environmental sound velocity.

Still alternatively, the sound velocity at the point of interest may be a local sound velocity at the point of interest. There are various method of finding this local sound velocity.

For example, a method of judging a local sound velocity value based on an optimum sound velocity value has been known, as described in Japanese Patent Application Laid-Open No. 2010-99452. In this method, first, based on an optimum sound velocity value at the point of interest, a waveform of a virtual-point received wave $W_X$ when the point of interest is assumed to be a reflection point is calculated. Next, an initial value of the assumed sound velocity at the point of interest is set, the assumed sound velocity is changed by one step, and a virtually-combined received wave $W_{SUM}$ obtained by virtually combining the received waves from a plurality of lattice points arranged equidistantly in an azimuth direction is calculated.

Next, an error between the virtual received wave $W_X$ and the virtually-combined received wave $W_{SUM}$ is calculated. The error between the virtual received wave $W_X$ and the virtually-combined received wave $W_{SUM}$ is calculated by using, for example, a method of taking a cross-correlation, a method of phase matching and adding by multiplying the virtual received wave $W_X$ by a delay obtained from the virtually-combined received wave $W_{SUM}$ or, conversely, a method of phase matching and addition by multiplying the virtually-combined received wave $W_{SUM}$ by a delay obtained from the virtual received wave $W_X$.

Here, to obtain a delay from the virtual received wave $W_X$, with the point of interest being taken as a reflection point, a time when the ultrasound wave propagating with the environmental sound velocity value at the point of interest arrives at each element is taken as a delay. Also, to obtain a delay from the virtually-combined received wave $W_{SUM}$, an equiphase line is extracted from a phase difference of the combined received waves between adjacent elements, and the equiphase line may be taken as a delay or a phase difference at maximum (peak) positions of the combined received waves of the respective elements may simply be taken as a delay. Furthermore, a cross-correlation peak position of the combined received waves from the respective elements may be taken as a delay. The error at the time of phase matching and addition is found by using, for example, a method of taking peak-to-peak of a waveform after matching and addition or a method of taking a maximum value of the amplitude after envelope detection.

Next, when operations by using all assumed sound velocity values are completed, a local sound velocity at the point of interest is judged. That is, an assumed sound velocity value with a minimum error between the virtual received wave $W_X$ and the virtually-combined received wave $W_{SUM}$ is judged as a local sound velocity value at the point of interest.

Also, as a method capable of measuring a local sound velocity even when the sound velocity of the object is non-uniform and the reception time (received wave) of each cannot be sufficiently approximated with the environmental sound velocity, the following method can be used.

For example, there is a method of finding, in advance, the point of interest in the region of interest and a reception time (a received wave) at a lattice point shallower than the point of interest and superposing the respective lattice received waves determined by the assumed sound velocity in the region of interest for combination to form a combined received wave, with which the received wave in the region of interest is compared, thereby judging a local sound velocity.

Alternatively, after the point of interest in the region of interest and a reception time (a received wave) at a lattice point shallower than the point of interest are found in advance, a minimum sum of the propagation time of the ultrasound wave from the point of interest to each lattice point determined by the assumed sound velocity in the region of interest and each lattice reception time for an element is taken as a combined reception time for that element, and the reception time at the point of interest and the combined reception time may be compared with each other to judge a local sound velocity.

Note that the point of interest and the reception time at the lattice point shallower than the point of interest can be found by using the image analyzing scheme and the phase aberration analyzing scheme described above.

For received signals of respective elements of the ultrasound probe, a phase difference therebetween is detected by taking the same signal as a reference signal, and phase difference detection results of adjacent elements are compared with each other and their difference is taken as D. On the other hand, in a graph with each element number of the ultrasound probe being plotted on the horizontal axis and each phase difference between the received signal of each element and a reference signal S being plotted on the vertical axis, 360° is added at discontinuities from positive to negative (that is, when the difference D above is smaller than −180°) and 360° is subtracted at discontinuities from negative to positive (that is, when the difference D above is larger than 180°), thereby changing a discontinuous curve to a continuous curve. With this, a wide range of phase aberration can be accurately detected (for example, refer to Japanese Patent Application Laid-Open No. 6-105841).

Also, another method to find a local sound velocity may be used as follows. For example, similarly to the above, after the reception time (received wave) of each lattice point shallower than the point of interest is found by the image analyzing and phase aberration analyzing schemes, the lattice received waves are superposed with a delay determined by an assumed sound velocity in the region of interest for combination to form a combined received wave. Based on a delay generated therefrom, an image is generated. That image is analyzed to judge a local sound velocity from a condition that, for example, sharpness is maximum.

An alternative method may be used as follows. After the reception time (received wave) of each lattice point is found, a minimum sum of the propagation time of the ultrasound wave from the region of interest to each lattice point with an assumed sound velocity in the region of interest and each lattice reception time for an element is taken as a delay for that element. Based on that delay, an image of the region of interest is generated. That image is analyzed to judge a local sound velocity from a condition that, for example, sharpness is maximum.

A still alternative method may be used as follows. Similarly to the above, the reception time (received wave) of each lattice point shallower than the point of interest is found by the image analyzing and phase aberration analyzing schemes. By taking the found time as a delay, the shallow lattice point described above is regarded as a virtual element. As a received signal of each virtual element, a signal obtained by matching and addition with each delay. From the reception signal of each virtual element, an image is generated based on an assumed sound velocity of the region of interest. That image is analyzed to judge a local sound velocity from a condition that, for example, sharpness is maximum.

Also, as a method of finding attenuation at the point of interest, for example, a method of finding attenuation by using each element's received signal before matching and addition can be thought as follows.

For example, transmission focus is performed to form pseudo point reflection and, by using each element's received data, from a change of the center frequency of the received signal in a depth direction after matching and addition with a center element or an aperture including the center element, a distribution of attenuation coefficients each per unit propagation time can be found. Alternatively, since the center frequency of each element's received signal has a value of the center frequency of the transmission wave shifted to a lower frequency side by an amount determined by attenuation in a propagation distance determined by the depth of the above pseudo point reflection and each element position, three unknowns, that is, the center frequency of the transmission wave, the depth of point reflection, and the attenuation coefficient, may be found from the center frequency of each element's received signal. Or, when the sound velocity of the above pseudo point reflection is found, the depth is simultaneously found, and the attenuation coefficient may be found with the center frequency of the transmission wave being assumed to be known.

To find the distribution of attenuation coefficients described above, a region of interest is first set, a predetermined number of transmission focuses are set along each line in the region of interest, relevant transmission focus is performed, and reception is made by each element. Next, a predetermined number of points regarding azimuth positions and depth positions in the region of interest are set, each element's transmission signal of transmission focus for each point of interest is selected, and a center frequency of a signal corresponding to the depth of the point of interest of a center element is found. This process is repeatedly performed for a depth position direction. A difference between center frequencies of the respective point of interests is taken in the depth direction, and the result is stored as an attenuation coefficient. This process is repeatedly performed for each azimuth position, thereby finding a distribution of attenuation coefficients each per unit propagation time. Alternatively, each element's received signal of transmission focus for each point of interest is selected, an unknown among the center frequency of the transmission wave, the depth of the point of interest, and the attenuation coefficient is assigned and an attenuation coefficient most suitably matching the center frequency of each element's received signal is stored as an attenuation coefficient at the point of interest. This process is repeatedly performed for each azimuth position, thereby finding a distribution of attenuation coefficients.

Also, to find a local attenuation coefficient from the center frequency of each element's received signal described above, a region of interest is first set, a predetermined number of transmission focuses are set along each line in the region of interest, relevant transmission focus is performed, and reception is made by each element. Next, a predetermined number of points regarding azimuth positions and depth positions in the region of interest are set, a local region with the points of interest set at the center of an upper surface is set, and a propagation path is set on a lower surface of the local region from each of the points of interest via each lattice to each element. Here, each propagation path can be found when a local sound velocity of the local region is found. Next, the center frequency of each element's received signal of transmission focus corresponding to the point of interest is reversely shifted along a path from each lattice to each element, thereby finding the center frequency at each lattice point on the lower surface of the local region. Here, a shift amount along the path from each lattice to each element can be separately found from each element's received signal obtained by performing transmission focus corresponding to each lattice. On the other hand, since the propagation path from lattice point of interest each lattice in the local region has been already found at the time of finding a local sound velocity, if the attenuation coefficient in the local region is assumed to be constant, the center frequency at each lattice point after propagation can be found from the center frequency at the lattice straight below the point of interest and the attenuation coefficient. And, the center frequency at the lattice straight below the point of interest can be separately found from each element's received signal obtained by performing transmission focus corresponding to the lattice straight below the point of interest. Therefore, an error between the center frequency at each lattice point found with an assumed attenuation coefficient and the center frequency at each lattice point found by reversely shifting the center frequency of each element's received signal of the point of interest is found, and an attenuation coefficient with which this error is minimum can be found as a true value. Even if the center frequency at the lattice straight below the point of interest is unknown, it is enough to adopt an attenuation coefficient when a center frequency at each lattice point obtained by assigning two unknowns, that is, the center frequency and the attenuation coefficient at the lattice straight below the point of interest, and the center frequency at each lattice point found by reversely shifting the center frequency most suitably match each other.

When each element's received data corresponding to the point of interest i and the local region are set as described above, a sound velocity or attenuation of the point of interest i is found by using each element's received data corresponding to each lattice point set on the lower surface of the local region. Note that how to set the lower surface of the local area and each lattice point is not particularly restrictive, and lattice points can be set on an any curved surface below the point of interest. For example, the lattice points may be set on a boundary between a tissue and a lesion.

Next, at step S150 of FIG. 3, the point-of-interest number i is incremented by 1 (1 is added to i). At the next step S160, it is determined whether i exceeds the number of points of interest (the predetermined number $i_0$).

As a result, if i has not exceed $i_0$ yet, the procedure returns to step S140, repeating the process of finding a sound velocity or attenuation at the point of interest i described above.

On the other hand, if it is determined that i exceeds $i_0$, the procedure goes to the next step S170.

At step S170, a variation index is found from a change in sound velocity or attenuation in the region of interest at each point of interest.

As the variation index, an index based on the magnitude of variation in sound velocity or attenuation at each point of interest can be used, for example, a standard deviation can be used. Alternatively, an index based on the spatial frequency of a change in sound velocity or attenuation in the region of interest at each point of interest, for example, a two-dimensional frequency distribution of sound velocity or attenuation, may be found, and the variation index may be found from the center frequency, band, or distortion of the index.

Other than that, various indexes with which non-uniformity can be evaluated can be thought as a variation index.

For example, as a histogram shape feature amount of a sound velocity or attenuation distribution in the region of interest and their spatial frequency distribution, skewness, kurtosis, or the like may be taken as a variation index. Alternatively, a texture feature amount from a cooccurrence matrix or the like, for example, uniformity, contrast, correlation, or entropy, may be used as a variation index.

Also, by not taking any of these feature amounts singly but from a plurality of feature amounts, a variation index may be found by using, for example, multiple regression.

By calculating an index representing a variation in sound velocity or attenuation (a variation index) in the manner described above, the tissue characteristic can be diagnosed with the use of this index.

For example, a large amount of data of specific lesions and their corresponding variations in sound velocity or attenuation are accumulated and, based on these data, a correspondence between values of the variation indexes and the states of tissue characteristics is statistically found, thereby setting a threshold of each variation index for diagnosing the tissue characteristic. Then, in actual diagnosis, a variation index is found by the method as described above, and is compared with the preset threshold, thereby diagnosing the tissue characteristic. With this, the tissue characteristic can be easily diagnosed.

As has been described above, according to the present embodiment, not an absolute value of sound velocity or attenuation in the region of interest but a variation (a variation index) is measured. Therefore, it is possible to grasp a microscopic change in sound velocity or attenuation structure due to a pathological change, the change being difficult to grasp with conventional measurement of an absolute value of sound velocity or attenuation, and the sonic or attenuation variation can be applied to diagnosis of a tissue characteristic.

While the ultrasound diagnostic device and the ultrasound diagnostic method according to the present invention have been described in detail above, the present invention is not restricted to the examples described above, and it goes without saying that various improvements and modifications may be performed in a range not deviating from the gist of the present invention.

REFERENCE SIGNS LIST

10 . . . ultrasound diagnostic device, 100 . . . CPU, 104 . . . display unit, 106 . . . data analyzing and measuring unit, 200 . . . operation input unit, 300 . . . ultrasound probe, 302 . . . ultrasound transducer, 400 . . . transmitting and receiving unit, 500 . . . image signal generating unit, 502 . . . signal processing unit, 506 . . . image processing unit

The invention claimed is:

1. An ultrasound diagnostic device comprising:
an ultrasound probe including a plurality of ultrasound transducers configured to transmit ultrasound waves to an object and to receive ultrasound waves reflected from the object to output an ultrasound detection signal; and
a computer configured to set a region of interest within the object and set points along each line along which each of said ultrasound waves is transmitted in the region of interest;
wherein the computer is configured to perform a predetermined number of transmission focuses of the ultrasound waves from the ultrasound probe along each line along which each of said ultrasound waves is transmitted in the region of interest to form a pseudo point reflection which includes transmitting said ultrasound waves and receiving reflected ultrasound waves from each of pseudo reflection sources that are focusing points of each of said transmission focuses; and
wherein the computer is configured to calculate a sound velocity or an attenuation with respect to each point of interest in the region of interest based on the received signal at each of the ultrasound transducers regarding the reflected ultrasound waves of the pseudo point reflection at the points in the region of interest; and
wherein the computer is configured to obtain a variation index indicating non-uniformity of a sound velocity or an attenuation in the region of interest based on a magnitude of a variation of said sound velocity or attenuation at each point of interest calculated according to said reflected ultrasound waves of the pseudo point reflection.

2. The ultrasound diagnostic device according to claim 1, wherein the computer is configured to perform said transmission focus of the ultrasound waves having a variation corresponding to each point of interest, to transmit the ultrasound waves from the ultrasound probe, and the ultrasound transducers receive reflected waves from each point of interest.

3. The ultrasound diagnostic device according to claim 1, wherein the computer is configured to receive reflected waves from a shallow point which is positioned in a region shallower than the point of interest with respect to a depth direction of the object by two or more of the ultrasound transducers, and to grasp the sound velocity or the attenuation in a local region including the point of interest and the shallow point based on the received signals at each of the ultrasound transducers from the point of interest and the received signals at each of the ultrasound transducers from the shallow point, and wherein the sound velocity or attenuation for each point of interest is the sound velocity and the attenuation in the local region.

4. The ultrasound diagnostic device according to claim 3, wherein the computer is configured to perform transmission focus of the ultrasound waves having a variation corresponding to each point of interest to transmit the ultrasound waves from the ultrasound probe, and the ultrasound transducers receive reflected waves from each point of interest and the shallow point.

5. The ultrasound diagnostic device according to claim 1, further comprising:
a display device configured to display a result of a calculation of the variation index.

6. The ultrasound diagnostic device according to claim 5, wherein said computer is configured to generate an amplitude image which represents an amplitude of the ultrasound detection signal with brightness of dots,
wherein the display device displays the result of the determination of the tissue characteristics as superposed on the amplitude image, or displays the amplitude image and the result of the calculation of the variation index which are arranged in a tiled manner.

7. The ultrasound diagnostic device according to claim 6, wherein
the computer switches a display mode between a first display mode in which the amplitude image is displayed alone and a second display mode in which the result of the calculation of the variation index is displayed, in accordance with an operation input from an operator accepted by the computer.

8. The ultrasound diagnostic device according to claim 5, wherein said computer is configured to generate an amplitude image which represents an amplitude of the ultrasound detection signal with brightness of dots,
wherein the display device displays the result of the calculation of the variation index by varying luminance in the amplitude image or coloring the amplitude image.

9. The ultrasound diagnostic device according to claim 8, wherein
the computer switches a display mode between a first display mode in which the amplitude image is displayed alone and a second display mode in which the result of the calculation of the variation index is displayed, in accordance with an operation input from an operator accepted by the computer.

10. A method in which an ultrasound diagnostic device including an ultrasound probe having a plurality of ultrasound transducers configured to transmit ultrasound waves to an object and to receive ultrasound waves reflected from the object to output an ultrasound detection signal, the method comprising the steps of:
setting a region of interest within the object and setting points along each line along which each of said ultrasound waves is transmitted in the region of interest using a computer;
performing a predetermined number of transmission focuses of the ultrasound waves from the ultrasound probe along each line along which each of said ultrasound waves is transmitted in the region of interest to form a pseudo point reflection at each of the points in the region of interest, said pseudo point reflection which includes transmitting said ultrasound waves and receiving reflected ultrasound waves from each of pseudo reflection sources that are focusing points of each of said transmission focuses;

calculating a sound velocity or an attenuation with respect to each point of interest in the region of interest based on received signals at each of the ultrasound transducers regarding the reflected ultrasound waves of the pseudo point reflection at the points in the region of interest; and obtaining a variation index indicating non-uniformity of a sound velocity or an attenuation in the region of interest based on a magnitude of a variation of said sound velocity or attenuation at each point of interest in the region of interest calculated according to the reflected ultrasound waves of the pseudo point reflection.

11. The method according to claim 10 in which the ultrasound diagnostic device performs a step of outputting a result of a calculation of the variation index to a display device.

12. The method according to claim 11 in which the ultrasound diagnostic device performs a step of displaying the result of the calculation of the variation index on the display device.

13. An ultrasound diagnostic device comprising:

an ultrasound probe including a plurality of ultrasound transducers configured to transmit ultrasound waves to an object and to receive ultrasound waves reflected from the object to output an ultrasound detection signal; and a computer configured to set a region of interest within the object and set points along each line along which each of said ultrasound waves is transmitted in the region of interest;

wherein the computer is configured to perform a predetermined number of transmission focuses of the ultrasound waves from the ultrasound probe along each line along which each of said ultrasound waves is transmitted in the region of interest to form a pseudo point reflection which includes transmitting said ultrasound waves and receiving reflected ultrasound waves from each of pseudo reflection sources that are focusing points of each of said transmission focuses; and wherein the computer is configured to calculate a sound velocity or an attenuation with respect to each point of interest in the region of interest based on the received signal at each of the ultrasound transducers regarding the reflected ultrasound waves of the pseudo point reflection at the points in the region of interest; and wherein the computer is configured to obtain a variation index indicating non-uniformity of a sound velocity or an attenuation in the region of interest based on a spatial frequency of a change in said sound velocity or attenuation at each point of interest calculated according to the said reflected ultrasound waves of the pseudo point reflection.

14. A method in which an ultrasound diagnostic device including an ultrasound probe having a plurality of ultrasound transducers configured to transmit ultrasound waves to an object and to receive ultrasound waves reflected from the object to output an ultrasound detection signal, the method comprising the steps of:

setting a region of interest within the object and setting points along each line along which each of said ultrasound waves is transmitted in the region of interest using a computer;

performing a predetermined number of transmission focuses of the ultrasound waves from the ultrasound probe along each line along which each of said ultrasound waves is transmitted in the region of interest to form a pseudo point reflection at each of the points in the region of interest, said pseudo point reflection which includes transmitting said ultrasound waves and receiving reflected ultrasound waves from each of pseudo reflection sources that are focusing points of each of said transmission focuses;

calculating a sound velocity or an attenuation with respect to each point of interest in the region of interest based on received signals at each of the ultrasound transducers regarding the reflected ultrasound waves of the pseudo point reflection at the points in the region of interest; and obtaining a variation index indicating non-uniformity of a sound velocity or an attenuation in the region of interest based on a spatial frequency of a change in said sound velocity or attenuation at each point of interest calculated according to the reflected ultrasound waves of the pseudo point reflection.

\* \* \* \* \*